United States Patent
Longo et al.

(10) Patent No.: US 6,696,407 B1
(45) Date of Patent: Feb. 24, 2004

(54) HUNTINGTON'S DISEASE TREATMENT COMPRISING ADMINISTERING ALDOSE REDUCTASE INHIBITORS TO INCREASE STRIATAL CNTF

(75) Inventors: Frank Longo, San Francisco, CA (US); Andrew Mizisin, Spring Valley, CA (US)

(73) Assignee: The Regents of the University of California, Oakland, CA (US)

( * ) Notice: Subject to any disclaimer, the term of this patent is extended or adjusted under 35 U.S.C. 154(b) by 582 days.

(21) Appl. No.: 09/045,194

(22) Filed: Mar. 20, 1998

Related U.S. Application Data

(63) Continuation-in-part of application No. 08/822,103, filed on Mar. 21, 1997, now abandoned.

(51) Int. Cl.[7] .................. A61K 31/00; A61K 31/44; A01N 43/42

(52) U.S. Cl. ................ 514/1; 514/298; 514/564

(58) Field of Search .............. 424/9.1, 9.2; 436/811; 514/564, 248, 1

(56) References Cited

U.S. PATENT DOCUMENTS

2002/0077319 A1 * 6/2002 Mylari .............. 514/217

FOREIGN PATENT DOCUMENTS

| EP | 0 002 895 A1 | 7/1979 | |
|---|---|---|---|
| EP | 0 059 596 A1 | 9/1982 | |
| WO | WO 92/16544 | 10/1992 | |
| WO | WO 93/15752 | * 8/1993 | .......... A61K/37/02 |

OTHER PUBLICATIONS

JP6–220055–A, Akinori et al., 8–09–1994 English Translation.*
JP4–182481–A, Kato et al., Jun. 30, 1992 English Translation.*
JP3–232851–A, Matsuo et al., Oct. 16, 1991 English Translation.*
JP61–56175–A, Niikata et al., Mar. 20, 1986 English Translation.*
The Huntington's Disease Collaborative Research Group (Mar. 26, 1993) "A novel gene containing a trinucleotide repeat that expanded and unstable on Huntington's disease chromosomes." Cell 72(6): 971–83.*
Ashizawa et al. (Jun. 1994) "CAG repeat size and clinical presentation in Huntington's disease." Neurology 44(6): 1137–43.*
Weigell–Weber et al. (Feb. 16, 1996) Psychiatric symptoms and CAG expansion in Huntington's disease. Am J Med Genet. 67(1): 53–7.*
Emerich et al. (Mar.–Apr. 1998) "Cellular Delivery of CNTF but not NT–4/5 prevents degeneration of striatal neurons in a rode model of Huntington's disease." Cell Transplant 7(2): 213–225.*
Stevens et al, Diabetologia 36: 608–614, 1993.*
Olin et al. (editor–in–chief: Olin BR), Drug Facts and Comparisons, p. 3210, 1995.*
Henderson, Progress in Neurobiology 48: 219–254, 1996.*
Goodman et al., The Pharmacological Basis of Therapeutics, 8th ed., pp. 1471–1475 and 1544, 1990.*
Cooper et al., The Biochemical Basis of Neuropharmacology, 6th ed., pp. 214 and 328–329, 1991.*
Hoyle et al., Biochem. Pharm., 44(2):231–41, Jul. 1992.*
Cameron et al., Br. J. of Pharm., 107(4):939–44, Dec. 1992.*
Taylor et al., Br. J. of Pharm., 111(1):42–8, Jan. 1994.*
Robinson et al., Diabetes, 35(3):295–99, Mar. 1986.*
Sredy et al., PNAS, 197(2):135–43, Jun. 1991.*
Calcutt et al., Pain, 58(3):413–20, Sep. 1994.*
Obrosova et al., Current Eye Res., 16(1):34–43, Jan. 1997.*
Apfel et al., "Effects of administration of ciliary neurotrophic factor on normal motor and sensory peripheral nerves in vivo" *Brain Res.* (1993) 604:1–6.
Anderson et al., "Ciliary neurotrophic factor protects striatal output neurons in an animal model of Huntington disease" *Proc. Natl. Acad. Sci. USA* (1996) 93:7346–7351.
Bhatnagar et al., "Aldose reductase: Congenial and injurious profiles of an enigmatic enzyme" *Biochem. Med. and Metabolic Biol.* (1994) 48:91–121.
Bird et al., "Why do DNA testing? Practical and ethical implications of new neurogenetic tests" *Ann. Neurol.* (1995) 38:141–146.
Beyer–Mears et al., "Zopolrestat prevention of proteinuria, albuminuria and cataractogenesis in diabetes mellitus" *Pharmacol.* (1996) 52:292–302.
Büyükbingöl et al., "Studies on the synthesis and structure–activity relationships of 5–(3'–indolal)–2–thiohydantoin derivatives as aldose reductase enzyme inhibitors" *Il Farmaco* (1994) 49(6): 443–447.
Calcutt et al., "Aldose reductase inhibition, Doppler flux and conduction in diabetic rat nerve" *Eur. J. Pharmacol.* (1994) 251:27–33.
Calcutt et al., "Inhibition of macrophage chemotaxis and peripheral nerve regeneration in normal and hyperglycemic rats by the aldose reductase inhibitor Tolrestat" *Exp. Neurol.* (1994) 128:226–232.

(List continued on next page.)

*Primary Examiner*—Gary Kunz
*Assistant Examiner*—Christopher James Nichols
(74) *Attorney, Agent, or Firm*—Morrison & Foerster LLP

(57) ABSTRACT

The present invention provides methods of modulating neurotrophic factor-associated activity, especially CNTF-associated levels and activity, using aldose reductase inhibitors. These methods are especially useful in individuals suffering from, or at risk of developing, neurological disorders, including neurodegenerative disorders. The invention also provides methods of palliating neurological disorders and delaying development of neurological disorders using aldose reductase inhibitors.

10 Claims, 5 Drawing Sheets

OTHER PUBLICATIONS

Calcutt et al., "Reduced ciliary neuronotrophic factor–like activity in nerves from diabetic or galactose–fed rats" *Brain Res.* (1992) 575:320–324.

Cameron et al., "Reversal of defective peripheral nerve conduction velocity, nutritive endoneurial blood flow, and oxygenation by a novel aldose reductase inhibitors, WAY–121,509, in streptozotocin–induced diabetic rats" *J. Diab. Comp.* (1996) 10:43–53.

Chien et al., "Saturable tissue binding and imirestat pharmacokinetics in rats" *Pharmaceutical Res.* (1992) 9(4):469–473.

Chomczynski et al., "Single–step method of RNA isolation by acid guanidinium thiocyanate–phenol–chloroform extraction" *Anal. Biochem.* (1987) 162:156–159.

Cook et al., "Kinetic characteristics of ZENECA ZD5522, a potent inhibitor of human and bovine lens aldose reductase" *Biochemical Pharmacol.* (1995) 49(8):1043–1049.

Cullum et al., "Glycation of rat sciatic nerve tubulin in experimental diabetes mellitus" *Diabetologia* (1991) 34:387–389.

Curtis et al., "Retrograde axonal transport of ciliary neurotrophic factor is increased by peripheral nerve injury" *Nature* (1993) 365:253–255.

Curtis et al., "Retrograde axonal transport of LIF is increased by peripheral nerve injury: Correlation with increased LIF expression in distal nerve" *Neuron* (1994) 12:191–204.

Davis et al., "Enzyme selectivity analyses of arylsulfonylamino acid aldose reductase inhibitors" (1993) *J. Enzyme Inhibition* 7:87–96.

Davis et al., "The molecular biology of the CNTF receptor" *Curr. Opin. Neurobiol.* (1993) 3:20–24.

de Waegh et al., "Local control of axonal properteis by Schwann cells: Neurofilaments and axonal transport in homologous and heterologous nerve grafts" *J. Neurosci. Res.* (1991) 30:201–212.

Dittrich et al., "Ciliary Neurotrophic Factor: Pharmacokinetics and Acute–Phase Response in Rat" *Ann. Neurol.* (1994) 35:151–163.

Dowton et al., "Diagnosis of human heritable diseases–Laboratory approaches and outcomes" *Clin. Chem.* (1995) 41:785–794.

Dyck et al., "Spatial pattern of nerve fiber abnormality indicative of pathologic mechanisms" *Am. J. Pathol.* (1984) 117:225–238.

Emerich et al., "Cellular delivery of human CNTF prevents motor and cognitive dysfunction in a rodent model of Huntington's disease" *Cell Transplantation* (1997) 6(3):249–266.

Emerich et al., "Implants of encapsulated human CNTF–producing fibroblasts prevent behavioral deficits and striatal degeneration in a rodent model of Huntington's disease" *J. Neurosci.* (1996) 16:5168–5181.

Emerich et al., "Protective effect of encapsulated cells producing neurotrophic factor CNTF in a monkey model of Huntington's disease" *Nature* (Mar. 1997) 386:395–399.

Fernyhough et al., "Altered neurotrophin mRNA levels in peripheral nerve and skeletal muscle of experimentally diabetic rats" *J. Neurochem.* (1995) 64:1231–1237.

Fernyhough et al., "Human recombinant nerve growth factor replaces deficient neutrophic support in the diabetic rat" *Eur. J. Neurosci.* (1995) 7:1107–1110.

Forcier et al., "Cellular pathology of the nerve microenvironment in galactose intoxication" *J. Neuropathol. Exp. Neurol.* (1991) 50:235–255.

Friedman et al., "Regulation of ciliary neurotrophic factor expression in myelin–related Schwann cells in vivo" *Neuron* (1992) 9:295–305.

Fujishima et al., "Improvement of corneal sensation and tear dynamics in diabetic patients by oral aldose reductase inhibitor, ONO–2235: a preliminary study" *Cornea* (1996) 15(4):368–372.

Greene et al., "A defect in sodium–dependent amino–acid uptake in diabetic rabbit peripheral nerve" *J. Clin. Invest.* (1990) 85:1657–1665.

Hellweg et al., "Endogenous levels of nerve growth factore (NGF) are altered in experimental diabetes mellitus: A possible role for NGF in the pathogenesis of diabetic neuropathy" *J. Neurosci. Res.* (1990) 26:258–267.

Hotta et al., "An aldose reductase inhibitor, TAT, prevents electroretinographic abnormalities and ADP–induced hyperaggregability in streptozotocin–induced diabetic rats" *Eur. J. Clin. Invest.* (1995) 25:948–954.

Hotta et al., "Effect of an aldose reductase inhibitor, SNK–860, on deficits in the electroretinogram of diabetic rats" *Exp. Physiol.* (1995) 80:981–989.

Hotta et al., "Effect of a potent new aldose reductase inhibitor, (5–(3–thienyl)tetrazol–1–yl)acetic acid (TAT), on diabetic neuropathy in rats" *Diabetes Res. and Clinical Practice* (1995) 27:107–117.

Hoyle et al., "Studies on the biochemical effects of the aldose reductase inhibitor 2,7–difluorospirofluorene–9, 5'–imidaxolidine–2',4'–dione (AL 1576, HOE 843)" *Biochemical Pharmacol.* (1992) 44(2):231–241.

Ip et al., "Ciliary neutrophic factor and its receptor complex" *Prog. Growth Factor Res.* (1992) 4:139–155.

Ip et al., "Injury–induced regulation of ciliary neurotrophic factor mRNA in the adult rat brain" *Eur. J. Neurosci.* (1993) 5:25–33.

Jakobsen, "Axonal dwindling in early experimental diabetes. I. A study of cross–sectioned nerves" *Diabetologia* (1976) 12:539–546.

Kador et al., "The pharmacology of aldose reductase inhibitors" *Ann. Rev. Pharm. Toxicol.* (1985) 25:691–714.

Kato et al., "Effect of long–term treatment with a new aldose reductase inhibitor, (2S,4S)–6–fluoro–2',5'dioxospiro–[chroman–4–4'imidazolidine]–2–carboxamide (SNK–860), on peripheral neuropathy in streptozotocin–induced diabetic rats" *J. Diab. Comp.* (1994) 8:27–32.

Lebo et al., "Multicolor in–situ hybridization and linkage analysis order charcot–marie–tooth type I (CMTIA) gene–region markers" *Am. J. Hum. Genet.* (1992) 50:42–55.

Longo et al., "Neuronotrophic activities accumulate in vivo within silicone nerve regeneration chambers" *Brain Res.* (1983) 261:109–117.

Longo, "Will ciliary neurotrophic factor slow progression of motor neuron disease?" *Ann. Neurol.* (1994) 36:125–127.

Manthorpe et al., "An automated colorimetric microassay for neuronotrophic factors" *Dev. Brain Res.* (1986) 25:191–198.

Manthorpe et al., "Ciliary neuronotrophic factor" *Neurotrophic Factors,* Louglin et al. eds. (1993), pp. 443–473.

Masson et al., "Aldose reductase inhibitors in the treatment of diabetic neuropathy" *Drugs* (1990) 39:190–202.

Matsui et al., "Pharmacological profiles of a novel aldose reductase inhibitors, SPR–210, and its effects on streptozotocin–induced diabetic rats" *Jpn. J. Pharmacol.* (1994) 64(2):115–124.

McLean et al., "Posttranlational modifications of nerve cytoskeletal proteins in experimental diabetes" *Mol. Neurobiol.* (1992) 6:225–237.

Miller et al., "A Placebo–controlled Trial of Recombinant Human Ciliary Neurotrophic (rhCNTF) Factor in Amyotrophic Lateral Sclerosis" *Ann. Neurol.* (1996) 39:256–260.

Mizisin et al., "Aldose Reductase Inhibition Increases CNTF–Like Bioactivity and Protein in Sciatic Nerves From Galactose–Fed and Normal Rats" *Diabetes* (1997) 46:647–652.

Mizisin et al., "Decreased endoneurial fluid electrolytes in normal rat sciatic nerve after aldose reductase inhibition" *J. Neurol. Sci.* (1993) 116:67–72.

Mizisin et al., "Schwann cell injury is attenuated by aldose reductase inhibition in galactose intoxication" *J. Neuropathol. Exp. Neurol.* (1993) 52:78–86.

Mizuno et al., "Effects of a new aldose reductase inhibitors, (2S,4S)–6–fluoro–2',5'–dioxospiro[chroman–4,4'–imidazolidine]–2–carboxamide (SNK–860), on the slowing of motor nerve conduction velocity and metabolic abnormalities in the peripheral nerve in acute streptozotocin–induced diabetic rats" *Metabolism* (1992) 41(10):1081–1086.

Nakayama et al., "Antihyperglycemic effects of M16209, a novel aldose reductase inhibitor, in normal and diabetic rats" *Eur. J. Pharmacol.* (1995) 276:77–83.

Nishimura et al., "Depletion of myo–inositol and amino acids in glactosemic neuropathy" *J. Neurochem.* (1987) 49:290–295.

Nukada et al., "Axonal caliber and neurofilaments are proportionately decreased in galactose neuropathy" *J. Neuropathol. Exp. Neurol.* (1986) 45:140–150.

Palo et al., "Enzyme and protein studies of demyelinatin in diabetes" *J. Neurol. Sci.* (1977) 33:171–178.

Pfeifer et al., "Perspective in Diabetes—Clinical trials of diabetic neuropathy: Past, Present, and Future" *Diabetes* (1995) 44:1355–1361.

Powell et al., "Abnormal nerve regeneration in galactose neuropathy" *J. Neuropathol. Exp. Neurol.* (1986) 45:151–160.

Powell et al., "Fine–structural localization of aldose reductase and ouabain–sensitive, K+–dependent, p–nitro–phenylphosphatase in rat peripheral nerve" *Acta Neuropathol.* (1991) 81:529–539.

Rende et al., "Immunolocalization of ciliary neuronotrophic factor in adult rat sciatic nerve" *Glia* (1992) 5:25–32.

Richard et al., "Tissue–specific effects of aldose reductase inhibition on fluorescence and cross–linking of extracellular matrix in chronic galactosemia" *Diabetes* (1991) 40:1049–1056.

Rodríguez–Peña et al., "Expression of neurotrophins and their receptors in sciatic nerve of expermientally diabetic rats" *Neurosci. Lett.* (1995) 200:37–40.

Ryle et al., "Non–enzymatic glycation of peripheral nerve proteins in human diabetics" *J. Neurol. Sci.* (1995) 129:62–68.

Saporito et al., "Chronic 1,25–dihydroxyvitamin $D_3$–mediated induction of nerve growth factor mRNA and protein in L929 fibroblasts and in adult rat brain" *Brain Res.* (1994) 633:189–196.

Scherer et al., "Axons modulate the expression of leukemia inhibitory factor by Schwann cells" *Soc. Neurosci. Abstr.* (1993) 19:246, Abstract 108.7.

Sendtner et al., "Ciliary neurotrophic factor prevents the degeneration of motor neurons after axotomy" *Nature* (1990) 345:440–441.

Sendtner et al., "Synthesis and localization of ciliary neurotrophic factor in the sciatic nerve of the adult rat after lesion and during regeneration" *J. Cell Biol.* (1992) 118:139–148.

Sensi et al., "Role of advanced glycation end–products (AGE) in late diabetic complications" *Diabetes Res. Clin. Practice* (1995) 28:9–17.

Sima et al., "Preventative effect of long–term aldose reductase inhibition (Ponalrestat) on nerve conduction and sural nerve structure in the spontaneously diabetic bio–breeding rat" *J. Clin. Invest.* (1990) 85:1410–1420.

Stöckli et al., "Molecular cloning, expression and regional distribution of rat ciliary neurotrophic factor" *Nature* (1989) 342:920–923.

Tanaka et al., "Enzymatic hydrolysis of zenarestat 1–O–acylflucuronide" *J. Pharm. Pharmacol.* (1994) 46:235–239.

Tanaka et al., "Toxicokinetics of zenarestat, an aldose reductase inhibitor in animals and man" *Xenobiotica* (1994) 24(5):461–71.

Tawata et al., "Anti–platelet action of isoliquiritigenin, an aldose reductase inhibitor in licorice" *Eur. J. Pharmacol.* (1992) 212:87–92.

Thoenen, H., "The changing scene of neurotrophic factors" *TINS* (1991) 14:165–170.

Thomas et al, "Amino acid uptake by dorsal root ganglia from streptozotocin–diabetic rats" *J. Neurol. Neurosurg. Psychiat.* (1984) 47:912–916.

Thomas et al., "Schwann–cell abnormalities in diabetic neuropathy" *Lancet* (1965) 1:1355–1357.

Thomas et al., "The pathology of diabetic neuropathy" *Quart. J. Med.* (1996) 35:489–509.

Tomlinson et al., "Aldose reductase inhibitors and diabetic complications" *Pharmacol. Ther.* (1992) 54:151–194.

Tsai et al., "Aldose reductase inhibitors: an update" *Annals of Pharmacother.* (1993) 27:751–754.

Unakar et al., "Effect of germanium–132 on galactose cataracts and glycation in rats" *Exp. Eye Res.* (1995) 61:155–164.

Williams et al., "High ciliary neuronotrophic specific activity in rat peripheral nerve" *Int. J. Dev. Neurosci.* (1984) 2:177–180.

Williamson et al., "Hyperglycemic pseudohypoxia and diabetic complications" *Diabetes* (1993) 42:801–813.

Wong et al., "Effects of ciliary neurotrophic factor (CNTF) on ventral spinal cord neurons in culture" *Soc. Neurosci. Abstracts* (1990) 16:484, Abstract No. 209.6.

Wuarin et al., "Early reduction in insulin–like growth factor gene expression in diabetic nerve" *Exp. Neurol.* (1994) 130:106–114.

Yagihashi et al., "Effects of long–term aldose reductase inhibition on development of experimental diabetic neuropathy. Ultrastructural and morphometric studies of sural nerve in streptozotocin–induced diabetic rats" *Diabetes* (1990) 39:690–696.

Yuen et al., "Therapeutic applications of neurotrophic factors in disorders of motor neurons and peripheral nerves" *Mol. Med. Today* (1995), pp. 278–286.

Dittrich, F. et al., "Ciliary Neurotrophic Factor: Pharmacokinetics and Acute–Phase Response in Rat" *Ann. Neurol.* 35:151–163 (1994).

Greene, D.A. and Sima. A.A.F., "Effects of Aldose Reductase Inhibitors on the Progession of Nerve Damage" *Diabetic Medicine* 10(Suppl 2):31S–32S (1993).

Jaspan, J.B. et al., "Clinical Studies with an Aldose Reductase Inhibitor in the Autonomic and Somatic Neuropathies of Diabetes" *Metabolism 35 Suppl. 1*(4):83–92 (1986).

Mizisin, A.P. et al., "Aldose Reductase Inhibition Increases CNTF–like Bioactivity and Protein in Sciatic Nerves From Galactose–Fed and Normal Rats" *Diabetes* 46:647–652 (1997).

Terada, M. et al., "Tolrestat Improves Nerve Regeneration After Crush Injury in Streptozocin–Induced Diabetic Rats" *Metabolism* 45(10):1189–1195 (1996).

* cited by examiner

HUNTINGTON'S DISEASE TREATMENT COMPRISING ADMINISTERING ALDOSE REDUCTASE INHIBITORS TO INCREASE STRIATAL CNTF

CROSS-REFERENCE TO RELATED APPLICATIONS

This application is a Continuation-in-Part of U.S. patent application Ser. No. 08/822,103, filed Mar. 21, 1997, now abandoned.

STATEMENT OF RIGHTS TO INVENTIONS MADE UNDER FEDERALLY SPONSORED RESEARCH

This invention was made in part during work supported by a grant from the Office of Research and Development (Medical Research Service) of the Department of Veterans Affairs (APM, NAC, FML) and a grant from the National Institutes of Health NS32339 (APM) and a grant from NIA (National Institute of Aging) AG09873 (FML). The government has certain rights in the invention.

TECHNICAL FIELD

This invention relates to neurotrophic factor-associated activity. More specifically, it relates to methods of modulating neurotrophic factor-associated activity using aldose reductase inhibitors (ARIs).

BACKGROUND

Use of neurotrophic factors, a class of growth factors that act on neurons, has gained considerable attention as potentially effective treatment of neurological disorders. Yuen et al. (1995) *Mol. Med. Today* 278–286. Neurotrophic factors have been shown to promote cell survival in vitro and to attenuate the behavioral and neurobiological consequences of central nervous system (CNS) damage in animal models of Alzheimer's, Parkinson's, and Huntington's diseases, amyotrophic lateral sclerosis (ALS) as well as peripheral nervous system (PNS) disorders including neuropathies. Neurotrophic factors also decrease damage due to trauma.

A serious problem with the concept of using neurotrophic factors in therapy has been delivery to neural tissue. These large, highly charged molecules are typically unable to penetrate the blood/brain barrier, thus hindering efforts to test efficacy in CNS disorders. At present, neurotrophic factors must be administered intrathecally (i.e., in cerebrospinal fluid), which involves technical obstacles and risk. Simpler modes of administration (such as subcutaneous) deliver only to motor neurons and the PNS. Even delivery within the PNS (across the blood/nerve barrier) can be problematic.

Ciliary neurotrophic factor (CNTF), a member of the neuropoietic cytokine family (which also includes leukemia inhibitory factor, interleukin 6, and oncostatin-M), is a protein of 200 amino acids. Manthorpe et al. (1993) in *Neurotrophic Factors*, Louglin et al. eds., 443–473. The CNTF gene has been cloned. Stockli et al. (1989) *Nature* 342:920–923: CNTF acts on ciliary ganglion and dorsal root ganglia (DRG) neurons, sympathetic neurons and motor neurons in the PNS. In the CNS, CNTF acts on several neuronal populations and has been shown to enhance survival of cultured hippocampal neurons and to prevent degeneration of injured medial septal neurons (cholinergic and non-cholinergic). In peripheral nerve, ciliary neurotrophic factor (CNTF) is present in abundance and has been localized to Schwann cells of myelinated fibers. Williams et al. (1984) *Int. J Dev. Sci.* 12:177–180; Rende et al. (1992) *Glia* 5:25–32; Friedman et al. (1992) *Neuron* 9:295–305. CNTF activity increases following injury and has been suggested to provide neurotrophic support to axons that facilitates neuronal survival and regeneration. Longo et al. (1983) *Brain Res.* 261:109–117; Thoenen (1991) *TINS* 14:165–170. Levels of CNTF-like activity in sciatic nerve are reduced after one to two months of hyperglycemia induced by galactose feeding or streptozotocin diabetes. Calcutt et al. (1992) *Brain Res.* 575:320–324.

CNTF has been indicated as having potential therapeutic potential for neurological disorders, such as neurodegenerative disease. Apfel et al. (1993) *Brain Res.* 604:1–6. However, as with neurotrophic factors in general, there have been serious problems associated with the administration of CNTF. Longo (1994) *Ann. Neurol.* 36:125–127; Yuen et al. (1995). Administration in animals has been accompanied by clear signs of toxicity, including fever, weight loss and induction of haptoglobin, an acute-phase protein, in the liver. Yuen et al. (1995). The short half-life of the molecule dictates high doses if administered exogenously, heightening the danger of toxicity and other possible undesirable cytokine-associated side effects. For example, in one clinical trial involving CNTF, a dose 30-fold lower than that demonstrated to produce a response in the Wobbler mouse was necessitated by intolerable side effects at higher doses. Miller et al. [(1996) *Ann. Neurol* 39:256–260] showed that the lack of efficacy of CNTF in treating ALS may have been caused in part by poor penetration of subcutaneously administered CNTF into the CNS, by its very short plasma half-life of 2.9 min in the context of only once daily administration [Dittrich et al. (1994) *Ann. Neurol.* 35:151–163], and/or by differences in the pathological mechanisms between ALS and animal models.

Several studies with CNTF have focused on transplantation of genetically modified cells releasing neurotrophic factors into normal or damaged brain regions, such as implants of encapsulated human CNTF-producing fibroblasts. Emerich et al. (1996) *J. Neurosci.* 16:5168–5181. However, strategies based on implants of genetically modified cells are limited by several factors, including host immune response, surgical risks associated with implantation, control of CNTF secretion, and lack of diffusibility of CNTF (i.e., the factor is localized to the site of implantation).

Several studies have suggested that CNTF protects striatal neurons in animal models of Huntington's disease (HD). Loss of medium-sized GABAergic striatal neurons was mediated by intrastriatal infusion of CNTF via osmotic pump, or implantation of a hCNTF-secreting, encapsulated fibroblast cell line, prior to injection of quinolinic acid. Implants also led to behavioral and cognitive protection. Anderson et al. (1996) *Proc. Natl. Acad. Sci. USA* 93:7346–7351; Emerich et al. (1996) *J. Neuroscience* 16:51–68–5181; Emerich et al. (1997) *Cell Transplantation* 6:249–266; Emerich et al. (1997) *Nature* 386:395–399. However, it remains unknown to what extent CNTF levels increased above endogenous levels in striatal tissue distant from the delivery source, and the use of implants of modified cells in treatments of HD is also subject to the limitations of implants described above.

A different area of research is the polyol pathway. The polyol pathway effects conversion of glucose to the polyhydric alcohol (polyol) sorbitol by the enzyme aldose reductase, followed by conversion of the sorbitol to fructose by sorbitol dehydrogenase. Kador et al. (1985) *Ann. Rev.*

*Pharm. Toxicity* 25:691–714; Bhatnagaretal. (1994) *Biochem. Med. and Metabolic Biol.* 48:91–121. Aldose reductase belongs to a family of NADPH-dependent oxidreductases, which are collectively known as aldehyde reductases.

In tissues which take up glucose independently of insulin and contain aldose reductase, the flux through the pathway under normal glycemic conditions is limited by the relatively low cellular glucose concentration and the low affinity of aldose reductase for glucose. Under these conditions glucose is metabolized predominantly by hexokinase. In hyperglycemia, however, glucose levels are elevated within these tissues, hexokinase is saturated and the fraction of glucose metabolized by aldose reductase increases.

Exaggerated flux through the polyol pathway has been implicated in the pathogenesis of biochemical, functional and structural nerve abnormalities associated with experimental diabetes (Tomlinson et al. (1992) *Pharmacol. and Therapeutics* 54:154–194). In peripheral nerve, aldose reductase (AR), the first enzyme of the polyol pathway, is localized to the Schwann cells of myelinated fibers. (Powell et al. (1991) *Acta Neuropathol.* 81:529–539) The ability of aldose reductase inhibitors (ARIs) to prevent structural and functional abnormalities of myelinated fibers (Yagihashi et al. (1990) *Diabetes* 39:690–696; Mizisin et al. (1993) *J. Neuropathol Exp. Neurol.* 52:78–86) suggests that flux through AR and/or polyol accumulation in Schwann cells may precipitate a variety of the nerve disorders reported in experimental diabetes. Aldose reductase inhibitors (ARI) have been studied extensively in the context of controlling complications of diabetes, such as neuropathy, nephropathy, retinopathy and cataracts. Tomlinson et al. (1992).

There exists a serious need for methods of providing neurotrophic factor-associated activity such as CNTF-associated activity to diseased or damaged neural tissue.

All publications cited herein are hereby incorporated in their entirety.

DISCLOSURE OF THE INVENTION

The present invention provides methods of modulating neurotrophic factor-associated activity using aldose reductase inhibitors (ARIs).

Accordingly, in one aspect, the invention provides methods of modulating neurotrophic factor-associated activity using an aldose reductase inhibitor, said method comprising administering an effective amount of an aldose reductase inhibitor to an individual. In some embodiments, the individual has a neurological disorder, such as a neurodegenerative disease. In other embodiments, the individual is at high risk for developing a neurological disorder, such as a neurodegenerative disease.

In some embodiments, the ARI is Ponalrestat. The neurotrophic factor-associated activity may be in the CNS and/or the PNS. In one embodiment, the modulated neurotrophic-associated activity is ciliary neurotrophic factor (CNTF).

In another aspect, the invention provides methods of palliating a neurological disorder which entail administering an effective amount of an ARI to an individual. In some embodiments, the ARI is Ponalrestat. In some embodiments, the neurological disorder is a neurodegenerative disorder.

In another aspect, the invention provides methods of delaying development of a neurological disorder which entail administering an effective amount of an ARI to a high risk individual. In some embodiments, the neurological disorder is a neurodegenerative disorder.

MODES FOR CARRYING OUT THE INVENTION

Figure 1:
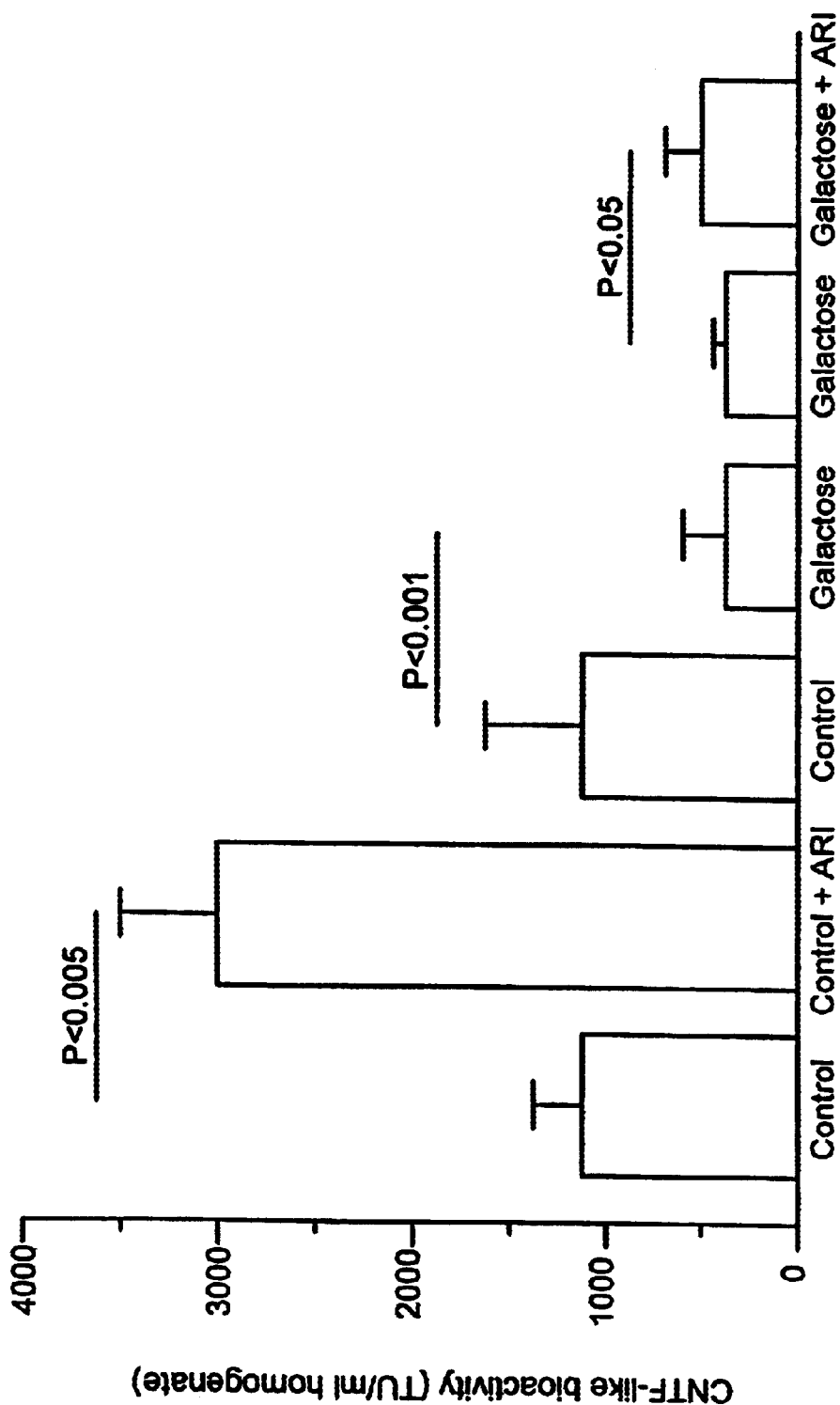
FIG. 1 is a bar graph depicting CNTF-like bioactivity in sciatic nerve homogenates from control rats (first and third bars); normal rats receiving ARI (second bar); galactose-fed rats (fourth and fifth bars); and galactose-fed rats receiving ARI (sixth bar).

We have discovered that administration of aldose reductase inhibitors (ARIs) modulates neurotrophic factor-associated activity in mammals. Normal rats receiving ARI Ponalrestat showed a surprising two and one-half fold increase of ciliary neurotrophic factor (CNTF) associated activity, as assessed (inter alia) by survival of neurons derived from embryonic chick ciliary ganglia, when compared to normal rats that did not receive any ARI. Further, we have found that rats receiving Tolrestat or Ponalrestat show significantly increased CNTF levels in striatal tissues. This observation is especially significant because this neural tissue is found in the brain, the site of many neurodegenerative disorders.

These methods are useful for a condition or circumstance in which neurotrophic factor-associated activity is indicated, such as neurological disorders, including neurodegenerative disorders. The methods can be used, for example, in Huntington's disease, amyotrophic lateral sclerosis (ALS), Alzheimer's disease, and Parkinson's disease, as well as with other neuropathies (including those due to heredity, toxicity, and/or trauma). The methods may also be useful in delaying development of a neurological disorder, and thus may be used in individuals who show no overt signs of disease but are, for example, at high risk of developing disease.

In one embodiment, the invention provides methods of modulating neurotrophic factor-associated activity that comprise administration of an effective amount of an ARI to an individual. As used herein, "neurotrophic factor-associated activity" means biological function(s) and/or aspect(s) associated with (i.e., in temporal and/or physical proximity to) one or more neurotrophic factors. Such activities include, but are not limited to, levels of neurotrophic factor(s) in tissues and/or cells, levels of mRNA(s) encoding neurotrophic factor(s), and various effector functions of the neurotrophic factor(s) itself, including neurogenerative activities. Examples of effector functions include, but are not limited to, cell survival (whether neural or non-neural), cell growth, maintenance (including anabolic and/or metabolic functions), differentiation, proliferation, development, regeneration, migration, delaying cell death (including apoptosis), receptor binding, events associated with receptor binding, such as phosphorylation and events associated with a signal transduction pathway, increase of neurotransmitter levels, and decrease in vulnerability to toxicity.

Neurotrophic factors are known in the art and include, but are not limited to, the neurotrophin family, such as nerve growth factor (NGF), brain-derived neurotrophic factor (BDNF), neurotrophin 3 (NT-3), and neurotrophin 4/5 (NT-4/5); the neurophoietic cytokine family, including ciliary neurotrophic factor (CNTF) and leukemia inhibitory factor (LIF or CDF/LIF); insulin-like growth factors, such as IGF-1 and IGF-2; transforming growth factor β (TGF-β) family, such as TGF-β1, TGF-β2, and glial-cell-line-derived neurotrophic factor (GDNF); fibroblast growth factor (FGF) family, such as FGF-1, FGF-2, and FGF-5; and other growth factors, such as transforming growth factor α, platelet-derived growth factor, and stem cell factor.

One skilled in the art will understand that a desired result of ARI administration may be bioactivity associated with presence of a neurotrophic factor, and that the desired end result may be an indirect, rather than a direct, result of presence of the neurotrophic factor per se. Thus, measuring the growth factor may be an indirect indicator of the desired end result, which may be, for example, neurogeneration, prolonged survival (i.e., preservation of neuronal viability), and/or optimized maintenance (i.e., maintenance which is enhanced when compared to lack of administration of an ARI).

In one embodiment, the neurotrophic factor is CNTF and the neurotrophic factor-associated activity is CNTF-associated activity. These activities include, but are not limited to, those mentioned above, particularly, promoting and/or prolonging cell survival and/or, regeneration, and delaying cell death. Accordingly, the invention provides methods of modulating CNTF-associated activity that comprise administration of an effective amount of an ARI to an individual. The invention also provides methods of modulating CNTF levels that comprise administration of an effective amount of an ARI to an individual. As used herein, "levels" of a neurotrophic factor, including CNTF, means the amount of bioavailable CNTF in a cell or in tissue. "Bioavailable" CNTF is CNTF or precursor molecules, such as mRNA. Levels of CNTF could increase by, for example, more protein production (whether general or specific), increased stability of CNTF (i.e., longer half-life), release of CNTF from a sequestered cellular location, and increased mRNA production or stability.

Levels of CNTF can be measured in blood, spinal fluid, or nerve biopsy using bioassays known in the art, such as ELISA. Such an assay is described in Example 1. Levels of CNTF mRNA can be measured using standard assays known in the art such as Northern analysis (Example 1). Activities associated with CNTF, such as enhancing cell survival, can be measured using standard in vitro assays (Example 1). Briefly, a cell homogenate (from, for example, an appropriate biological sample such as a nerve biopsy) is cultured in vitro with ganglia (typically derived from chick embryos). Cell survival is measured using methods known in the art such as dye exclusion and compared to cell survival of untreated control. Increased cell survival indicates CNTF-associated activity. Alternatively, CNTF-associated activity (as with other neurotrophic factors) can be assessed by receptor binding. Ip et al. (1992) *Prog. Growth Factor Res.* 4:1–17; Davis et al. (1993) *Curr. Opin. in Neurobiol.* 3:20–24. For example, the Trk family of receptor—linked tyrosine kinases are high affinity neurotrophic receptors. Events occurring downstream of receptor binding, such as phosphorylation, can be detected using in vitro phosphorylation assays known in the art.

It is evident to one skilled in the art that the above description of functional assays of CNTF activity and assays designed to indicate levels of CNTF per se are applicable to other neurotrophic factors, and likewise descriptions for each factor need not be cataloged herein, as these techniques are readily available and adaptable.

As used herein, an "individual" is a vertebrate, preferably a mammal, more preferably a human. Mammals include, but are not limited to, farm animals, sport animals, and pets.

The individual may be normoglycemic. A "normoglycemic" individual is one who has normal blood glucose levels. "Normoglycemic" is a term well-understood in the art and reflects a blood glucose level understood in the clinical arts to be in the normal, i.e., not hyper or hypo, levels. Normal levels are usually standardized according to the particular method used to measure blood glucose levels. Methods of measuring glucose parameters are well known and include, but are not limited to, glucose meters, so-called test strips, hemoglobin A1a, A1b, A1a+b, and other spectrophotometric assays. Glucose levels can be measured in blood, plasma, serum, urine, and other body fluids.

The individual may also be adjudged to have a "non-diabetes condition". As used herein, an individual who has a "non-diabetes" condition is one who is clinically assessed to not have diabetes, either type I or type II. Diabetes is a known clinical condition and reflects a state in which overall glucose levels are not regulated properly, i.e., are generally too high, due to absolute or relative insulin deficiency, either due to insufficient insulin production (such as in type I, or insulin-dependent diabetes) or due to inability of insulin to properly regulate glucose levels (such as in type II, or non-insulin-dependent diabetes). Diabetes is assessed using standard clinical parameters, more typically chronic blood glucose levels. Standards exist in the clinical arts for determining at which glucose levels an individual is considered to have diabetes. It is understood that, once an individual has been adjudged to have diabetes, this individual is still considered to have diabetes (and thus is not classified has having a non-diabetes condition) even though one or more measurements of blood glucose indicates normal levels, unless the individual has received a procedure designed to correct the defect in glucose regulation, such as islet transplantation, and no longer requires administration of medications and/or hormone designed to correct the defect in glucose regulation, such as insulin or medications for type II diabetes.

For purposes of this invention, an individual suitable for administration of ARI(s) is one who is likely, or may, benefit from increased levels of neurotrophic factor-associated activity. Such an individual is one who either has developed, or is at high risk of developing, a neurological disorder(s). A "neurological disorder" as used herein means an aberration from clinically normal neural cell activity (i.e., compromised neural cell activity) and includes, but is not limited to, neurodegenerative disease (of the CNS and/or PNS), neuropathies associated with toxicity (neurotoxicity) such as chemotherapy (i.e., vincristine or cisplatin-induced motor neuropathy) and alcohol consumption, immune-mediated neurodiseases such as multiple sclerosis (MS) and Guillain-Barre syndrome, hereditary neuropathies such as Charcot-Marie-Tooth neuropathies [Lebo et al. (1992) *Am. J. Hum. Genet.* 50:42–55], injury due to trauma, and compromised function due to senescence. Thus, "neurological disorder"

encompasses not only disease conditions, but also other conditions in which neural function is compromised, due to physical and/or chemical alterations, whether caused endogenously (as with a hereditary disorder) or exogenously (as with an externally caused trauma). Examples of neurodegenerative disorders include but are not limited to, Huntington's disease, amyotrophic lateral sclerosis (ALS), Alzheimer's disease, Parkinson's disease, and Shy-Drager syndrome.

It is understood that neurological disorders affect mammals other than human, and thus this invention may find use in administration to, for example, farm animals, sports animals, and pets, as the definition of "individual" encompasses. It is also understood, as stated above, that the methods disclosed herein would also be suitable for any context in which a neurotrophic factor, preferably CNTF, is shown to exert a positive or desirable effect, even if this effect is on cell types other than neural cells.

Development or high (i.e., significant) risk of developing a neurological disorder is indicated by any of a number of established clinical parameters, depending on the disorder. Individuals adjudged at "significant risk" or "high risk" of developing a neurological disorder will be discussed in detail below.

The effect of neurotrophic factor-associated activity (such as CNTF activity) may be exerted in the central nervous system (CNS; brain and spinal cord) or the peripheral nervous system (PNS; motor, sensory, autonomic nerves and nerves outside the brain and spinal cord), including the motor neurons. Thus, the methods described herein are applicable to neurological disorders, including neurodegenerative diseases, that affect the CNS (such as Parkinson's, Huntington's and Alzheimer's disease) as well as those that affect the PNS as well as the CNS, such as ALS and Shy-Drager syndrome. The methods described herein also are applicable to neurological disorders that affect the PNS, such as chemotherapy-associated neuropathies, nerve trauma, lower motor neuron diseases, and Charcot-Marie-Tooth neuropathies. Accordingly, the invention includes methods of modulating neurotrophic factor-associated activity (including CNTF-associated activity) in the CNS. The invention also includes methods of modulating neurotrophic factor-associated activity (including CNTF-associated activity) in the PNS (including motor neurons). The invention also provides methods of modulating neurotrophic factor associated activity (including CNTF-associated activity) in the CNS and/or PNS.

The ARI used can be any of those known in the art, or any compound shown to inhibit the enzyme aldose reductase. Inhibition of aldose reductase can be measured by standard in vitro assays known in the art. Pharmaceutical grade ARIs are available from a variety of commercial vendors. Examples include Tolrestat, N-[[6-methoxy-5-(trifluoromethyl)-1-naphthalenyl]thioxomethyl]-N-methylglycine, [Wyeth-Ayerst, Princeton, N.J.; other designations are Tolrestatin, CAS Registry Number 82964-04-3, Drug Code AY-27,773, and brand names ALREDASE (Am. Home) and LORESTAT (Recordati)]; Ponalrestat, 3-(4-bromo-2-fluorobenzyl)-4-oxo-3H-phthalazin-1-ylacetic acid [ICI, Macclesfield, U.K.; other designations are CAS Registry Number 72702-95-5, ICI-128,436, and STATIL (ICI)]; Sorbinil, (S)-6-fluoro-2,3-dihydrospiro[4H-1-benzopyran-4,4'-imidazolidine]-2',5'-dione (Pfizer, Groton, Conn.; CAS Registry Number 68367-52-2, Drug Code CP-45,634); EPALRESTAT (ONO, Japan); METHOSORBINIL (Eisal); ALCONIL (Alcon); AL-1576 (Alcon); CT-112 (Takeda); AND-138 (Kyorin). Other ARIs have been described. For a review of ARIs used in the diabetes context, see Humber, Leslie "Aldose Reductase Inhibition: An Approach to the Prevention of Diabetes Complications", Porte, ed., Ch. 5, pp. 325–353; Tomlinson et al. (1992) Pharmac. Ther. 54:151–194), such as spirohydantoins and related structures, spiro-imidazolidine-2',5'-diones; and heterocycloic alkanoic acids. Other aldose reductase inhibitors are ONO-2235; Zopolrestat; SNK-860; 5-3-thienyltetrazol-1-yl (TAT); WAY-121,509; ZENECA ZD5522; M16209; (5-(3'-indolal)-2-thiohydantoin; zenarestat; zenarestat 1-O-acylglucuronide; SPR-210; (2S,4S)-6-fluoro-2',5'-dioxospiro-[chroman-4,4'-imidazolidine]-2-carboxamide (SNK-880); arylsulfonylamino acids; 2,7-difluorospirofluorene-9,5'-imidazolidine-2',4'-dione (imiriestat, Al11576, HOE 843); isoliquiritigenin.

As used herein, an "effective amount" is an amount effective to effect a desired and/or beneficial result. An effective amount can be administered in one or more administrations. For purposes of this invention, an effective amount is an amount sufficient to enhance or increase (i.e., modulate) neurotrophic factor-associated activity. Such modulation may have desirable concomitant effects, such as to palliate, ameliorate, stabilize, reverse, slow or delay progression of a neurological disorder, or delay or even prevent development (onset) of a neurological disorder.

The amount of the ARI administered will depend on several variables, such as the particular ARI used, the time course of administration, the condition of the individual, the desired objective, the extent of disease, how many doses will be administered, and whether any other substances are being administered. Generally, the amount used will be as recommended by the manufacturer and/or based on empirical studies. The amount of a single administration may be about 50 to about 1000 mg per kg body weight, or about 50 to about 1000 mg per day. The amount of a single administration can be about 5, about 10, about 20, about 25, about 50, about 100, about 125, about 150, about 200, about 250, about 300, about 350, about 400, about 450, about 500, about 550, about 600, about 650, about 700, about 750, about 800, about 850, about 900, about 950, about 1000, about 1500, or about 2500 mg per day. With respect to Tolrestat, the amount of a single administration can be about 10, about 15, about 25, about 50, about 100, about 200, about 400, about 500, about 1000, about 1500 or about 2000 mg per day. Alternatively, the amount of a single administration can be from about 5 to 10 mg, from about 10 to 25 mg, from about 25 to about 75 mg, from about 50 to about 150 mg per day, from about 100 to about 250 mg, from about 150 mg to about 300 mg, from about 200 mg to about 350 mg, from about 250 mg to about 400 mg, from about 300 mg to about 500 mg, from about 400 mg to about 750 mg, from about 800 mg to about 1000 mg per day. With respect to Sorbinil, the amount of a single administration can be about 100 to about 250 mg per day. Alternatively, the amount of a single administration can be about 50, about 75, about 100, about 150, about 200, about 250, about 300, about 350, about 400, about 450, about 500, about 550, about 600, about 750, about 1000 mg per day. With respect to ONO-2235, the amount of a single administration can be about 10, about 25, about 50, about 75, about 100, about 150, about 250, about 500, or about 750 mg per day. Rats are generally given about doses in terms of mg per kg body weight, and the amount of a single administration can be about 1, about 2, about 4, about 5, about 8, about 10, about 25, about 30, about 50, about 100, or about 150 mg/kg, generally per day. Any of these daily doses can be further subdivided into separate administrations.

Preferably, the ARI is Ponalrestat or Tolrestat, although any ARI shown to effect the desired neurotrophic factor-associated activity may be used. If either of these ARIs is used, the amount of a single administration can be about 10, about 25, about 50, about 100, about 150, about 200, about 250, about 300, about 350, about 400, about 500, about 750, about 1000, or about 1500 mg per day. Preferably, the dose is about 300 mg per day. Alternatively, the amount of a single administration may be about 25 to about 75 mg per day, about 50 to about 75 mg per day, about 75 to about 100 mg per day, about 100 to about 150 mg per day, about 125 to about 200 mg per day, about 150 to about 225 mg per day, about 200 to about 250 mg per day, about 225 to about 275 mg per day, about 250 to about 300 mg per day, about 275 to about 350 mg per day, about 325 to about 375 mg per day, about 350 to about 400 mg per day, about 400 to about 450 mg per day, about 450 to about 500 mg per day, or about 500 to about 1000 mg per day. Any of these daily doses can be further subdivided into separate administrations.

"Modulating" neurotrophic factor-associated activity means that the level, amount, and/or duration of neurotrophic factor-associated activity (such as CNTF-associated activity) is altered. Generally, for purposes of this invention, "modulating" neurotrophic activity means that the level, amount, and/or duration is enhanced, or increased, when compared to the level, amount, and/or duration in that individual when no ARI is administered. As is evident to one skilled in the art, however, within the context of administering ARIs, modulation may also mean a decrease in neurotrophic activity; for example, if an ARI dose is altered such as that level of activity drops from that of the previous (i.e., before the alteration) dose.

Preferably, an ARI is administered in a suitable pharmaceutical excipient. Pharmaceutical excipients are known in the art and are set forth in *Remingtons' Pharmaceutical Sciences*, 18th edition, Mack Publishing (1990).

For the methods described herein, an ARI(s) is preferably administered to an individual orally. Other routes of administration include, but are not limited to, injection. An ARI may also be administered via a delivery vehicle, such as a patch or an osmotic pump. It may also be desirable to administer an ARI via buccal administration, particularly using a device which allows continuous administration of the ARI. Administration can be given as a bolus (i.e., complete release), or can be time-released, using formulations and devices known in the art. The interval between administration(s) of an ARI(s) can vary and will depend, inter alia, on the neurological disorder being treated, the method of administration (i.e., whether in bolus or time-release) and the responsiveness of the individual.

An ARI may be administered alone, or in conjunction with other substances and/or therapies, depending on the context of administration (i.e., desired end result, condition of the individual, and indications). "In conjunction with" means that an ARI is administered prior to, concurrently, or after the other substance or therapy. It is also possible that different ARIs will exert different, sometimes complementary, neurotrophic-associated activities, and one ARI may be more suitable in a particular context (such as, for example, a particular neural cell type or part of the brain) than another. On the other hand, one or more ARIs may be interchangeable, depending on the context. These empirical determinations can be made by one skilled in the art by administering an ARI and measuring and/or localizing neurotrophic factor levels and/or associated activity, such as is described in Examples 1 and 2. Other examples of substances that might be administered in conjunction with an ARI include, but are not limited to, neurotrophic factors, cytokines, and other substances that are believed to be effective in treating and/or preventing development of a neurological disorder, such as drugs, vitamins, acetylcholine esterase inhibitors (particularly for Alzheimer's disease), L-dopa (particularly for Parkinson's disease), co-enzyme Q (particularly for Huntington's disease), excitatory amino acid receptor blockers (particularly for Huntington's disease), and agents designed to inhibit free radical damage.

The invention also provides methods of palliating a neurological disorder, such as a neurodegenerative disorder, which entail administration of an effective amount of an ARI to an individual. "Palliating" a neurological disorder means that the extent and/or undesirable clinical manifestations are lessened and/or time course of the progression is slowed or lengthened, as compared to not administering an ARI. "Palliation" includes, but is not limited to, alleviation of symptoms, diminishment of extent of disease, stabilized (i.e., not worsening) state of disease, delay or slowing of disease progression, and remission (whether partial or total) whether detectable or undetectable. Neurological disorders, including neurodegenerative disorders, are known in the art and examples have been provided above.

The invention also provides methods of delaying development of a neurological disorder, such as a neurodegenerative disorder, which entail administering an effective amount of an ARI to a high risk individual. "Development" of a neurological disorder means initial manifestations and ensuing progression of the disorder. Development of a neurological disorder can be detectable and assessed using standard clinical techniques, such as measuring neural function. However, development also refers to disease progression that may be undetectable. For purposes of this invention, progression refers to the biological course of the disease state. "Development" includes occurrence, recurrence, and onset. As used herein "onset" or "occurrence" of a neurological disorder includes initial onset and/or recurrence.

As is evident to one skilled in the art, delaying the development and/or progression of a neurological disorder can apply to those individuals not displaying any symptoms. As used herein, "delaying" development of a neurological disorder means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of a neurological disorder is a method that reduces the probability of disease development in a given time frame and/or reduces extent of the disease in a given time frame, when compared to not using the method. Such comparisons are typically based on clinical studies, suing a statistically significant number of subjects, although this knowledge can be based upon anecdotal evidence. Neurological disorders, including neurodegenerative diseases, are known in the art and examples have been provided above.

A "high risk" individual is an individual who has a discrete and significant risk of developing azneurological disorder. A "high risk" individual may or may not have detectable disease, and may or may not have displayed detectable disease prior to receiving the method(s) described herein. "High risk" denotes that an individual has one or more so-called risk factors, which are measurable parameters that correlate with development of a neurological disorder. An individual having one or more of these risk factors has a higher probability of developing a neurological disorder than an individual without these risk factor(s). These risk factors include, but are not limited to, history of previous disease, presence of precursor disease, genetic (i.e., hereditary) considerations (including family history and genetic markers), presence or absence of appropriate chemical markers, exposure to toxins such as certain chemotherapeutic agents, previous nervous system trauma, and indicators revealed by various imaging modalities, such as CT scan, MRI, and PET, which are used, inter alia, to assess status of striatum and other regions.

For example, DNA testing can indicate presence of an abnormal gene that predicts eventual development of Huntington's disease. Bird et al. (1995) *Ann. Neurol.* 38:141–146; Dowton et al. (1995) *Clin. Chem.* 41:785–794. DNA testing also indicates possibility of developing familial forms of ALS. Presence of an apoE susceptibility gene indicates proclivity to development of Alzheimer's disease. DNA testing also reveals proclivity to developing Charcot-Marie-Tooth neuropathies. Administration of certain chemotherapeutic agents, such as cisplatin and vincristine, are known to increase risk of developing neuropathy. Excessive alcohol consumption places an individual at risk of developing neuropathy, especially if there has been a family history of the disorder(s). Presence of certain antibodies could indicate risk of developing a neuropathy due to an auto-immune disorder. All of the above examples are indicators of risk (as well as others known in the art and yet to be developed), and any one or a combination may be taken into account in determining whether an individual is a suitable candidate for administration of an ARI in this context.

A high risk individual has one, preferably two, more preferably three, risk factors. However, it is understood that having only one risk factor can often indicate high risk; for example, carrying the Huntington's disease gene puts that individual at high risk of developing Huntington's disease, regardless of whether any other risk factor(s) may or may not be present.

Because all risk factors for developing neurological disorders are not known, and the interplay among these factors (in terms of overall risk) are not fully understood, it is clear to one skilled in the art that individuals suitable for administration of ARI for purposes of this invention can have clinical features in common, and that individuals not falling clearly in the categories described above can nonetheless be considered suitable candidates for administration of ARI(s). For example, an individual having a genetic marker for development of a neurodegenerative disorder (such as the apoE gene) could be considered at risk for developing Alzheimer's disease, even though no previous disease has been observed. In this context, administration of ARI to such an individual could result in delay of occurrence of disease, even to the extent that the individual does not develop the disease within his or her lifetime (or develops it later than would have been expected). Another example is an individual who is being treated using other modes of therapy, and who is showing clinical responsiveness to the therapy (i.e., remission). Such an individual may be adjudged as at "high risk" even though the initial course of therapy is not yet completed, due to projection of clinical progress by the clinician, and can be a suitable candidate for receiving an ARI(s) before completion of the initial therapy. The clinician, as one skilled in the art, has discretion to determine whether treatment using an ARI may be indicated.

An ARI may be administered alone or may also be used in conjunction with other substances and/or therapies (whether established or experimental) that serve to enhance and/or complement an ARI's effectiveness. Examples of such substances have been provided above and include, but are not limited to, other ARI(s), cytokines, medications used to treat Parkinson's disease, such as L-dopa, medications used to treat Huntington's disease, such as co-enzyme Q and excitatory amino acid receptor blockers, medications used to treat Alzheimer's disease, such as acetylcholine esterase inhibitors, and agents designed to inhibit free radical damage. ARI administration may be used to complement these and other therapies, either concomitantly or serially with respect to other therapies. The sequence and timing of these administrations can be determined empirically and will depend on such variables as the disease being treated, the condition of the individual, clinical history and indications, and/or responsiveness to various therapies. Such determinations are within the skill of the art.

In order to determine the effect of ARI administration, an individual may be monitored for disease (or precursor disease) progression as well as biochemical and/or genetic markers of disease (or precursor disease). With respect to disease progression, multiple rating scales (i.e., indices of clinical function) have been established and are known in the art for neurological disorders, particularly neurodegenerative diseases, such as the Huntington's scale and the Appel ALS rating scale. Nerve function can be tested, inter alia, by electrophysiological (conduction) testing and testing of various motor and/or cognitive functions. Imaging modalities such as CT scan, MRI, and PET may be used to assess status of various neural regions, such as the spinal cord, striatum, and other regions of the brain. Alternatively, as described above and in Example 1, the level of neurotrophic factor, such as CNTF, can be measured by detection (by ELISA, for example) in blood, serum, spinal fluid, and/or nerve biopsy.

The following examples are provided to illustrate but not limit the invention.

EXAMPLES

Example 1

Effect of Administration of ARI on CNTF Activity in Rats

Experimental Design and Assays

These studies were conducted with the approval of the San Diego Veterans Administration Animal Studies Subcommittee. Female Sprague-Dawley rats (240–300 g; Charles River, San Diego, Calif.) were housed in cages with wire bottoms to reduce contact with urine and feces. Groups were established and fed either a 40% D-galactose diet or a control diet specially formulated by Purina that contained 40% solka floc, a nonnutritive fiber, to balance nutritional intake. All diets contained 100% of the micronutrients required by rats and, with water, were available ad libitum. Each of these diet groups contained animals that were treated with the ARI, Ponalrestat (50 mg/kg), daily by oral gavage. After two months, rats were anesthetized by intraperitoneal injection (1 ml/kg ip) of pentobarbital sodium (12.5 mg/ml) and diazepam (1.25 mg/ml) in bacteriostatic saline. Under deep anesthesia, motor nerve conduction velocity (MNCV) was measured in the left hindlimb prior to removal of the sciatic nerve. The proximal portion was processed for subsequent light microscopic examination and the distal portion used for gas chromatographic analysis of nerve polyols. The contralateral sciatic nerve was removed and used for assay of CNTF-like neurotrophic activity and either Northern blot or ELISA analysis of CNTF mRNA or protein, respectively.

MNCV measurements were made with nerve temperature maintained at 37° C. (Calcutt et al., (1994) *Eur. J. Pharmacol.* 251:27–33). A 58019 Square Wave Stimulator (Stoelting Co, Chicago, Ill.) was used to deliver suprathreshold, monophasic electrical stimuli (50 V amplitude and 50 μs duration) to an active electrode inserted first at the ankle and then at the sciatic notch. Evoked responses were recorded with needle electrodes placed in the interosseous muscles of the ipsilateral foot, amplified (×100) with a P15 AC Amplifier (Grass Instruments Co, Quincy, Mass.) and recorded on a 5110 Storage Oscilloscope and 5D10 Waveform Digitizer (Tektronix, Inc., Beaverton, Oreg.). This procedure was repeated three times for each nerve. The distance between stimulation sites with the hindlimb extended was divided by the median latency difference between responses evoked from the ankle and sciatic notch to calculate MNCV.

For determination of water content and dry weight, distal segments of sciatic nerve were lightly blotted, weighed prior to freeze-drying and reweighed. Nerve polyols were measured by gas chromatography with α-methylmannoside as an internal standard (Mizisin et al., (1993) *J. Neurol. Sci.* 116:67–72) using a Hewlett Packard 5890 gas chromatograph (Hewlett Packard, Avondale, Pa.) fitted with a flame ionization detector and a 25 m×0.2 mm capillary column (Hewlett Packard Ultra 1). Nerve water and polyol contents are expressed as mg and nmol per mg nerve dry weight, respectively.

Bioassays were performed on extracts of sciatic nerve as described previously by Calcutt et al. (1992) *Brain Res.* 575:320–324. Briefly, 4 mm segments were homogenized in cold Hank's balanced salt solution, centrifuged and the soluble supernatant aspirated. An aliquot of the supernatant was used to determine the amount of protein using the Bradford assay. The remaining supernatant was used to assay CNTF-like activity by the ability to support the 24 hour survival of day eight embryonic chick ciliary ganglia ($E_8CG$) neurons. $E_8CG$ neurons were obtained from chick ciliary ganglia after trypsin treatment and trituration in Dulbecco's Modified Eagle's Medium plus 10% fetal calf serum (DMEM+10% FCS). After seeding onto a tissue culture dish for 2.5 hours to allow attachment of nonneuronal cells, unattached neurons were collected, counted and added to 96-well microtiter plates (500 neurons/well) precoated with polyornithine and laminin. Nerve homogenates were serially diluted in DMEM+10% FCS, added to the microtiter plates and incubated for 24 hours. A dose-response curve using rat recombinant CNTF was used as a standard and to establish the maximum CNTF effect for each assay. For the final 6 hours of incubation, cultures were exposed to the vital dye MTT (3-(4,5-diaminothiazol-2-yl)-2,5-diphenyl tetrazolium bromide) using the protocol of Manthorpe et al. ((1986) *Dev. Brain Res.* 25:191–198). Cells were then fixed and the number of surviving, intact, blue-staining cells counted using phase contrast microscopy. For each dilution, values in duplicate wells were averaged. Three different bioassays were conducted. In the first, aliquots of 10 control and 10 control+ARI nerve homogenates were bioassayed. In the second, aliquots of the control group were bioassayed again with aliquots of 10 nerve homogenates from the galactose group. In the third bioassay, aliquots of the galactose nerve homogenates were bioassayed again with aliquots of 10 nerve homogenates from the galactose+ARI group. Neurotrophic activities of the nerve homogenates are expressed in trophic units/ml (TU/ml). A trophic unit is defined as the dilution of nerve extract that supports 50% of the maximum survival promoted by CNTF.

The specificity of the bioassay for CNTF-like activity was verified with 0036, a neutralizing polyclonal anti-rat CNTF antibody (Regeneron, Tarrytown, N.Y.) raised against rat rCNTF and concentrated by ammonium sulfate precipitation. Ten mm segments of three sciatic nerves were homogenized in 300 μl of phosphate-buffered saline and diluted for bioassay using a modification of the procedure described above. Briefly, 3,000 $E_8CG$ neurons were plated in half-area 96-well plates. Aliquots of each homogenate and aliquots of a rCNTF standard (1 ng/ml) were added to $E_8CG$ neurons in the presence of 0, 3, 10, 30, or 100 μg/ml of the neutralizing CNTF antibody, 0036. MTT was added for the final 4 hours of incubation after which the cells and MTT crystals were solubilized. Plates were then read spectrophotometrically and the optical density of triplicate readings averaged.

CNTF mRNA levels in sciatic nerve were obtained by first homogenizing 1 cm segments of nerve on ice for 30 seconds in 4 M guanidine thiocyanate containing 0.1 M β-mercaptoethanol, 25 mM sodium citrate and 0.5% sarcosyl (pH 7.0). Total RNA was then isolated by the method of Chomczynski and Sacchi ((1987) *Anal. Biochem.* 162:156–159). Ten μg of each sample was separated on 1% agarose/2% formaldehyde gels stained with ethidium bromide to localize 28S and 18S ribosomal RNA and transferred to nylon membranes (Pharmacia, Piscataway, N.J.). Membranes were hybridized with a rat CNTF cDNA probe or a rat glyceraldehyde phosphate dehydrogenase (GAPDH) cDNA probe, both of which were random prime labeled with [$^{32}P$]dCTP (Ip et al., (1993) *Eur. J. Neurosci.* 5:25–33). The membranes were then exposed to XAR-5 autoradiographic film (Kodak, Rochester, N.Y.) for various times at −80° C. with an intensifying screen. Autoradiographic bands were quantified using an Ultrascan XL laser densitometer (LKB, Uppsala, Sweden). Ratios of CNTF:GAPDH were determined using optical densities in the linear range for both probes.

CNTF protein was determined with an ELISA that utilizes a monoclonal capture antibody which recognizes a non-C-terminal epitope on both rat and human CNTF (Regeneron, Tarrytown, N.Y.). The captured CNTF was recognized by a polyclonal rabbit anti-rCNTF reporter antibody. An alkaline phosphatase-tagged goat anti-rabbit IgG was used to generate the signal. In practice, 96-well Immulon plates were coated with capture antibody overnight, then blocked and washed. After overnight incubation of standards and samples, plates were washed and reporter antibody added. Following final washes, the reaction was developed using the GIBCO BRL ELISA amplification system substrate and amplifier. The reaction was stopped with 0.5 N $H_2SO_4$ and the plates read at two wavelengths (490 nm and 650 nm).

For light microscopic examination, proximal portions of sciatic nerve were fixed in 2.5% phosphate-buffered glutaraldehyde (490 mosmol/kg $H_2O$). Tissue was then post-fixed in 1% aqueous osmium tetroxide for 3 to 4 hours before dehydration using a series of graded alcohols and propylene oxide. After infiltration with a 1:1 mixture of propylene oxide and araldite for 4 hours, nerves were placed in 100% araldite overnight before embedding in fresh araldite resin. Thick sections (1 μm) were cut with glass knives and stained with p-phenylenediamine prior to light microscopic examination.

In each animal, computer-assisted analysis of the axonal size-frequency distributions of myelinated fibers was performed on a single thick section sampled from the tibial fascicle midway between the sciatic notch and popliteal fossa as described in detail previously by Forcier et al. (1991) *J. Neuropathol. Exp. Neurol.* 50:235–255. Briefly, video images (Cohu, San Diego, Calif.) of the tibial fascicle obtained with an Olympus light microscope were analyzed using a VAXstation II/GPX processor (Digital Equipment Corp., Boston, Mass.) with data translation imaging hardware (DT 2651, Data Translation, Marlboro, Mass.) for digitization of single video frames and an image processing board (DT2658) for mathematical operations. Axonal areas surrounded by myelin sheaths of myelinated fibers greater than 1 μm in diameter were identified and sorted with an automated process into bins based on axonal diameter. Approximately 2,000 myelinated fibers per tibial fascicle were examined.

All experiments and data collection were conducted with animals and tissue coded to minimize bias. The possibility of a difference in the means of two groups was tested with a two-tailed, unpaired t test. However, when standard deviations were unequal, a potential difference in the medians of two groups was tested with the Mann-Whitney test. The possibility of differences occurring between three groups was tested by one way ANOVA and, if a statistically significant difference was found (P<0.05), multiple comparisons were made with the Student-Newman-Keuls test. However, when significant differences between groups variances were detected by Bartlett's test, data were analyzed by Krukal-Wallis nonparametric ANOVA and Dunn's post-hoc test. Unless otherwise noted, all data are presented as mean ±SD.

Results

The effect of two months of galactose feeding and ARI treatment on body weight, nerve water and polyol content, and MNCV is shown in Table 1. Data are presented as mean ±SD (N=8 to 10) and were analyzed with a one way ANOVA after which multiple comparisons were made with the Student-Newman-Keuls test. Mean dulcitol levels were compared with an unpaired, two-tailed t test. Control and animals received a diet containing 0% D-galactose and galactose animals a diet containing 40% D-galactose for two months. ARI-treated animals received a daily oral gavage (50 mg/kg) of Ponalrestat (ND—Not detected).

The impact of galactose intoxication and the effect of ARI treatment on CNTF-like bioactivity of sciatic nerve is illustrated in FIG. 1. In the untreated galactose-fed group, CNTF-like bioactivity (TU/ml) was significantly reduced to 30% of that assayed in the control group (P<0.001). Although ARI treatment significantly increased CNTF-like bioactivity by 60% compared to the untreated galactose group (P<0.05), it was not restored to control levels.

Bioactivity in ARI-treated control animals was increased by nearly 250% compared to untreated control animals. Similar patterns were seen when CNTF-like bioactivity was expressed as TU/mg protein. In a concentration-dependent manner, the neutralizing antibody, 0036, blocked bioactivity in the rCNTF (kindly provided by the University of California at San Diego; now commercially available) standard as well as CNTF activity in the nerve extracts. At a concentration of 100 μg/ml, the average bioactivity remaining in the recombinant standard was 11% of that measured without neutralizing antibody. At the same concentration of 0036, the average remaining bioactivity in the nerve extracts was 5.3±2.7% (N=3) of that measured without this neutralizing antibody.

Figure 2:
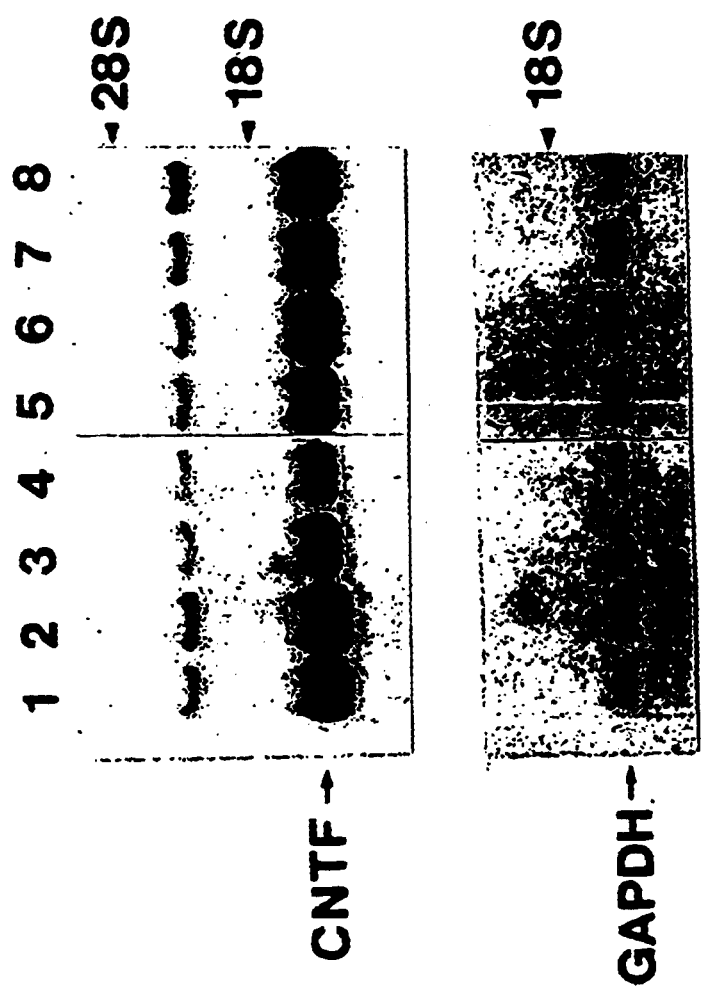
FIG. 2 is a half-tone reproduction of an autoradiogram depicting mRNA levels of CNTF in sciatic nerves from untreated and ARI-treated control and galactose-intoxicated rats.

The expression of sciatic nerve CNTF mRNA as detected by Northern blot analysis is shown in FIG. 2. In contrast to CNTF-like bioactivity, galactose intoxication and ARI treatment had no marked effect on the level of CNTF message expression of CNTF:GAPDH ratios.

Figure 3:
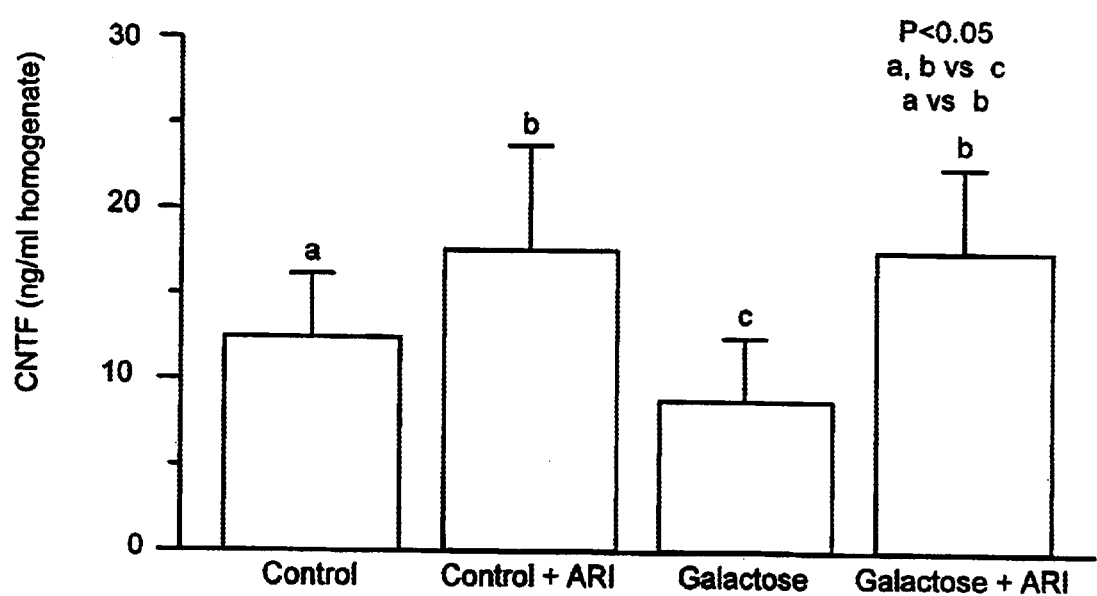
FIG. 3 is a bar graph depicting CNTF protein levels as detected by ELISA in sciatic nerves from control rats (first bar); normal rats receiving ARI (second bar); galactose-fed rats (third bar) galactose-fed rats receiving ARI (fourth bar).

CNTF protein levels in sciatic nerve were determined with a sensitive two-site ELISA (FIG. 3). Compared to the untreated control group, CNTF levels were decreased by 25% in the untreated galactose group (P<0.05). ARI treatment increased the amount of CNTF detected by ELISA by 50% in both control and galactose-fed animals relative to untreated control rats (both P<0.05).

Figure 4:
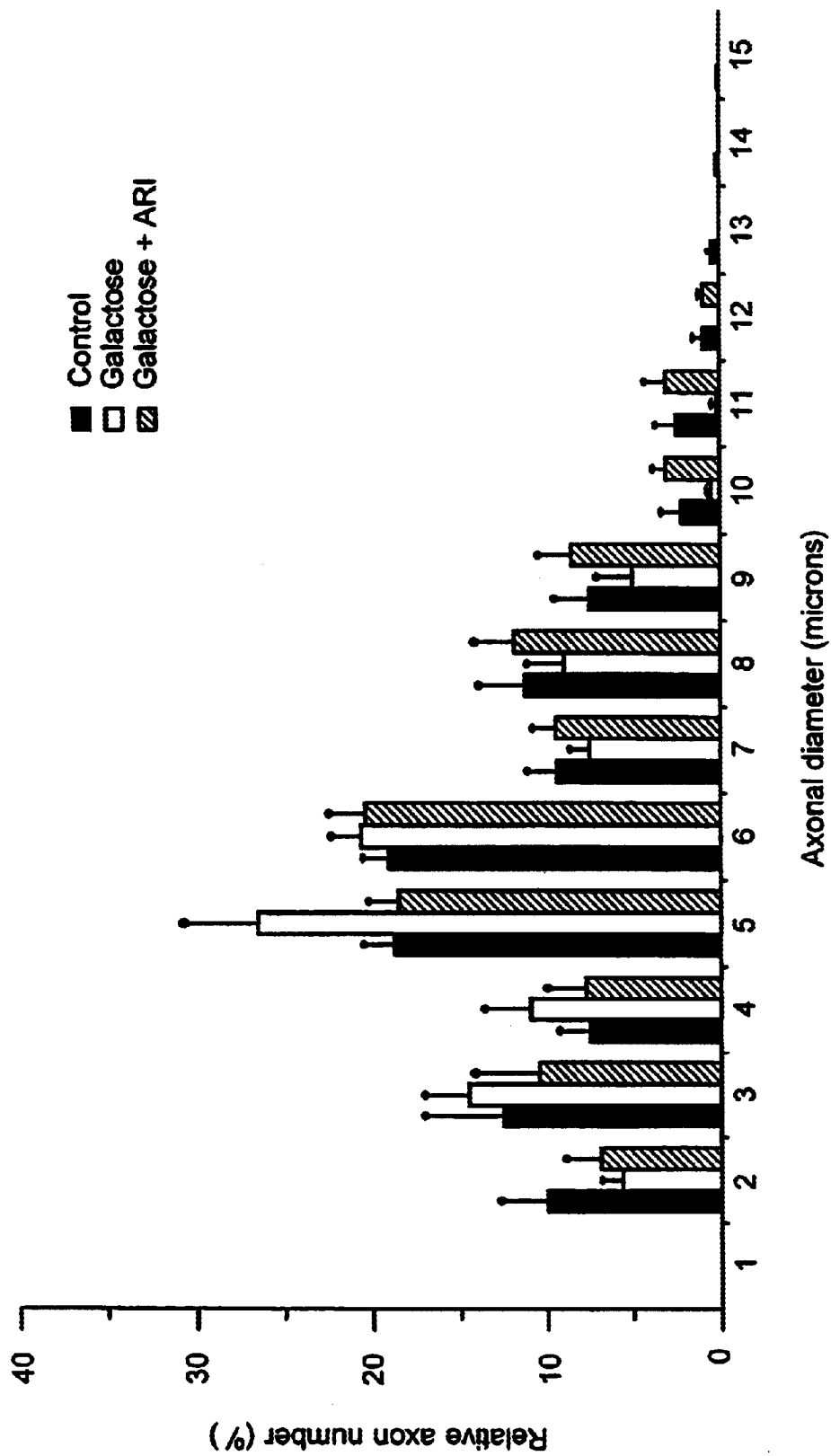
FIG. 4 is a bar graph depicting the effect of ARI treatment on the axonal size-frequency distribution of myelinated fibers in sciatic nerves in control rats (solid bar), galactose-fed rats (open bar), and galactose-fed rats receiving ARI (hatched bar).

Two months of galactose feeding was associated with a shift in the axonal size-frequency distribution of myelinated fibers towards those with smaller diameter axons (FIG. 4). This shift in size-frequency distribution was reflected as a decrease in the relative number of large fibers and a concomitant increase in the number of medium-sized fibers as shown in Table 2. Changes in axonal caliber were prevented

TABLE 1

Body weight, sciatic nerve water and polyol content, and motor nerve conduction velocity (MNCV) after two months of galactose intoxication and the effect aldose reductase inhibitor (ARI) treatment.

| Group | Body wt. (g) | Water (mg/mg dry wt) | Dulcitol (nmol/mg dry wt) | myo-Inositol (nmol/mg dry wt) | MNCV (m/s) |
|---|---|---|---|---|---|
| Control | 321 ± 15$^a$ | 1.7 ± 0.2$^a$ | ND | 9.3 ± 1.5$^a$ | 67.3 ± 4.0$^a$ |
| Control + ARI | 289 ± 19$^b$ | 1.8 ± 0.1$^a$ | ND | 12.3 ± 1.5$^b$ | 63.9 ± 4.0$^a$ |
| Galactose | 272 ± 18$^c$ | 2.5 ± 0.3$^b$ | 51.9 ± 11.0 | 4.7 ± 0.8$^c$ | 58.2 ± 5.5$^b$ |
| Galactose + ARI | 291 ± 14$^b$ | 1.8 ± 0.3$^a$ | 12.2 ± 3.8 | 9.4 ± 1.9$^a$ | 64.8 ± 5.1$^a$ |
|  | P < 0.05 | P < 0.001 | P < 0.0001 | P < 0.001 | P < 0.05 |
|  | a, b vs c | a vs b |  | a, b vs c | a vs b |
|  | a vs b |  |  | a vs b |  |

Compared to the untreated and ARI-treated control groups, the body weight of the galactose group was decreased and nerves from galactose-fed animals had increased water content, dulcitol accumulation and myo-inositol depletion. Treatment of galactose-fed rats with the ARI, Ponalrestat, restored nerve water and myo-inositol content to normal levels, and attenuated dulcitol accumulation. MNCV was significantly reduced in galactose-fed rats compared to untreated control and ARI-treated control and galactose-fed animals (P<0.05).

by ARI treatment. Data are presented as the mean ±SD (N=8 to 10 per group) and were analyzed with a one way ANOVA after which multiple comparisons were made with the Student-Newman-Keuls test. Myelinated axons with diameters ≤3 μm, >3 μm but <7 μm or ≥7 μm were classified as small, medium and large, respectively. Control animals received a diet containing 0% D-galactose and galactose animals a diet containing 40% D-galactose for two months. ARI-treated animals received a daily oral gavage (50 mg/kg) of Ponalrestat (NS—not significant).

TABLE 2

Relative number of small, medium and large myelinated axons in sciatic nerve after two months of galactose intoxication and the effect of ARI treatment.

| Group | Relative number (%) | | |
| --- | --- | --- | --- |
| | Small | Medium | Large |
| Control | 22.7 ± 6.2 | 43.5 ± 4.2[a] | 33.8 ± 6.7[a] |
| Galactose | 19.7 ± 4.1 | 58.2 ± 5.9[b] | 22.1 ± 5.2[b] |
| Galactose + ARI | 17.7 ± 4.9 | 45.2 ± 5.0[a] | 37.1 ± 6.7[a] |
| | NS | $P < 0.001$ a vs b | $P < 0.001$ a vs b |

EXAMPLE 2

Effect of Administration of ARI on Striatal CNTF Levels in Rats

Figure 5:
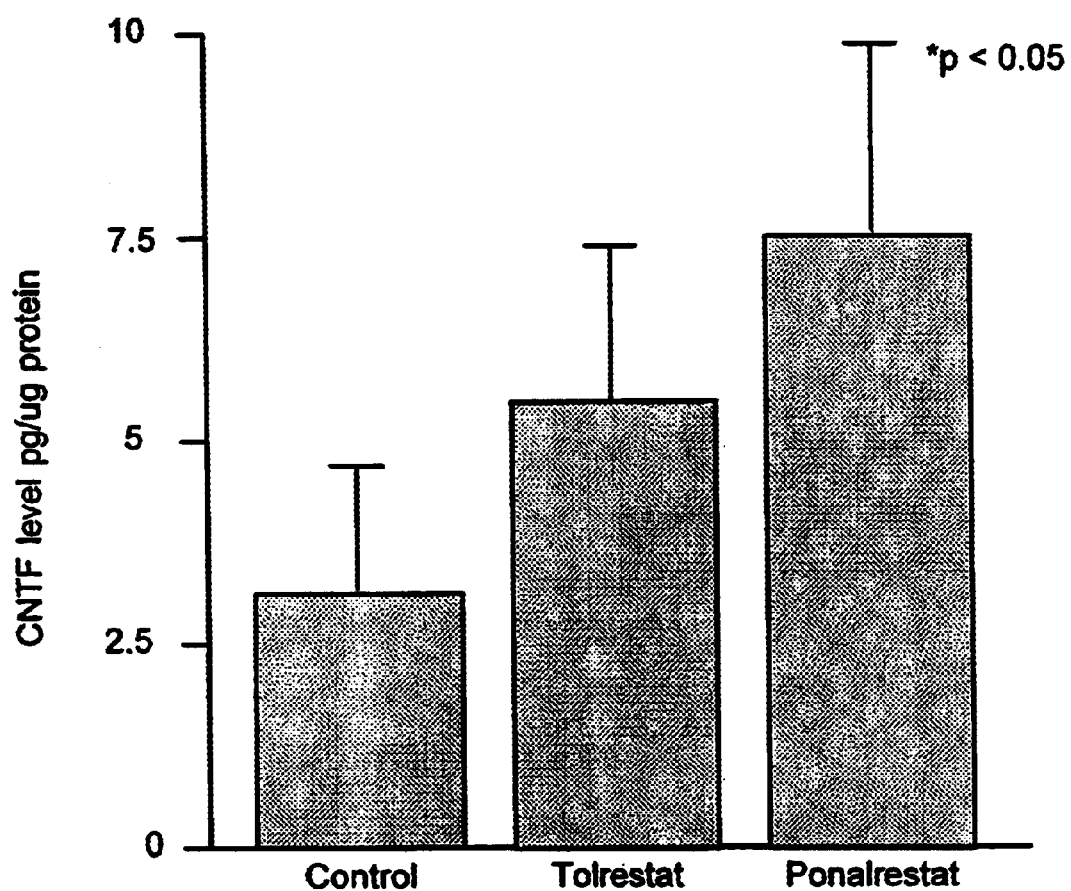
FIG. 5 is a bar graph depicting CNTF bioactivity in striatal tissue in control rats (first bar), and rats receiving Tolrestat (second bar) or Ponalrestat (third bar).

ARIs Toirestat and Ponalrestat were orally administered to adult rats at a dose of 50 mg/kg/day for two months as described in Example 1 and in Mizisin et al (1997) *Diabetes* 46: 647–652. For each rat, the left and right striatum were dissected and combined for homogenization in phosphate buffered saline. CNTF levels in extract preparations were then measured by ELISA, as described in Example 1. Four rats served as controls, and five rats each received Tolrestat and Ponalrestat. Five ELISA assays were run for each rat and one mean value derived for each rat. Mean values±SEM for each group of rats as a percentage of the control group are shown in FIG. 5. Since the standard deviations between the treatment groups were significantly different, the nonparametric Mann-Whitney test was used rather than the student t test.

As shown in FIG. 5, both ARIs demonstrated an increase in striatal CNTF activity level. Tolrestat caused an approximately two-fold increase in striatal CNTF activity level, and Ponalrestat, an approximately three-fold increase.

These results demonstrate that oral administration of ARIs modulates CNTF levels in brain tissue.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. A method of increasing levels of endogenous ciliary neurotrophic factor (CNTF) comprising administering an effective amount of an aldose reductase inhibitor to a norinoglycermic individual having Huntington's disease, wherein an effective amount is sufficient to increase the levels of ciliary neurotrophic factor in the striatum of said individual.

2. The method of claim 1, wherein said aldose reductase inhibitor is 3-(4-bromo-2-fluorobenzyl)-4-oxo-3H-phthalazin-1-ylacetic acid.

3. The method of claim 1, wherein said aldose reductase inhibitor is N-[[6-methoxy-5-(trifluoromethyl)-1-napthalenyl]thioxomethyl]-N-methylglycine.

4. The method of claim 1, wherein the increased levels of CNTF prolongs cell survival.

5. The method of claim 1, wherein the increased levels of CNTF delays cell death.

6. A method of increasing levels of endogenous ciliary neurotrophic factor (CNTF) comprising administering an effective amount of an aldose reductase inhibitor to a normoglycemic individual at high risk of Huntington's disease, wherein an effective amount is sufficient to increase the levels of ciliary neurotrophic factor in the striatum said individual.

7. The method of claim 6, wherein said aldose reductase inhibitor is 3-(4-bromo-2-fluorobenzyl)-4-oxo-3H-phthalazin-1-ylacetic acid.

8. The method of claim 6, wherein said aldose reductase inhibitor is N-[[6-methoxy-5-(trifluoromethyl)-1-napthalenyl]thioxomethyl]-N-methylglycine.

9. The method of claim 6, wherein increased levels of CNTF prolongs cell survival.

10. The method of claim 6, wherein increased levels of CNTF delays cell death.

* * * * *